United States Patent
Bettuzzi et al.

(10) Patent No.: US 7,994,216 B2
(45) Date of Patent: Aug. 9, 2011

(54) STAGE-SPECIFIC REDUCTION OF LUTS IN PROSTATE DISEASE

(75) Inventors: Saverio Bettuzzi, Montecchio Emilia (IT); Arnaldo Corti, Pontecchio Marconi (IT)

(73) Assignee: Genprofiler, S.R.L., Bolzano (IT)

( * ) Notice: Subject to any disclaimer, the term of this patent is extended or adjusted under 35 U.S.C. 154(b) by 138 days.

(21) Appl. No.: 11/972,892

(22) Filed: Jan. 11, 2008

(65) Prior Publication Data

US 2008/0214659 A1    Sep. 4, 2008

Related U.S. Application Data

(63) Continuation-in-part of application No. 11/658,614, filed as application No. PCT/IB2005/002107 on Jul. 21, 2005.

(60) Provisional application No. 60/884,760, filed on Jan. 12, 2007.

(51) Int. Cl.
    *A61K 31/35* (2006.01)
(52) U.S. Cl. .................................................. 514/456
(58) Field of Classification Search ............ 514/456
    See application file for complete search history.

(56) References Cited

U.S. PATENT DOCUMENTS 5,605,929 A    2/1997    Liao et al.
7,070,816 B2    7/2006    Newmark et al.

OTHER PUBLICATIONS

Bettuzzi et al. Cancer Res., vol. 66, No. 2, Jan. 15, 2006, pp. 1234-1240.*
Roehrborn, C.G. Rev. Urol., 2004, vol. 6, No. 3, pp. 121-127.*
Gupta et al. PNAS, 2001, vol. 98, pp. 10350-10355.*
Chow et al. Clinical Cancer Research, 2005, vol. 11, No. 12, pp. 4627-4633.*
Pytel et al. Urologiia, 2004, vol. 2, pp. 3-7 (Abstract attached).*
Lowe et al. Current Prostate Reports, 2004, vol. 2, pp. 133-136.*
Chow, H-H. Sherry, Pharmacokinetics and Safety of Green Tea Polyphenols after Multiple-Done Administration of Epigallacatechin Gallate and Polyphenon E in Healthy Individuals, Clinical Cancer Research, Aug. 15, 2003, vol. 9, pp. 3312-3319, National Cancer Institute, Bethesda, Maryland.
Khan M.D., Masood A., Chemoprevention and Prostate Cancer, Reviews in Urology, 2003; 5(1): 61-63, Med Reviews, LLC.
Steiner, Mitchell S., Phase IIA Clinical Trial to Test the Efficacy and Safety of Toremifene in Men with High-Grade Prostatic Intraepithelial Neoplasia, , Clinical Prostate Cancer, vol. 2, No. 1, 24-31, 2003.
Price, David, Toremifene for the Prevention of Prostate Cancer in Men With High Grade Prostatic Intraepithelial Neoplasia: Results of a Double-Blind, Placebo Controlled, Phase IIB Clinical Trial, The Journal of Urology, vol. 176, pp. 965-971, Sep. 2006, The American Urological Association.

* cited by examiner

*Primary Examiner* — James Anderson
(74) *Attorney, Agent, or Firm* — Fish & Associates, PC

(57) ABSTRACT

Methods and compositions are presented in which catechin-containing compositions have statistically significant and strong therapeutic effect in the treatment of LUTS wherein such compositions are stage-specifically administered to a patient diagnosed with HG-PIN and optional coexistent BPH.

8 Claims, No Drawings

STAGE-SPECIFIC REDUCTION OF LUTS IN PROSTATE DISEASE

This application is a continuation-in-part of our co-pending U.S. patent application with the Ser. No. 11/658,614, which was filed Jan. 12, 2007 as a national phase application of PCT/IB05/02107, which was filed Jul. 21, 2005 and which is incorporated by reference herein, and further claims priority to our U.S. provisional patent application with the Ser. No. 60/884,760, which was filed Jan. 12, 2007.

FIELD OF THE INVENTION

The field of the invention is treatment of prostate disease and associated symptoms, and especially reduction of lower urinary tract symptoms (LUTS) in patients with high-grade prostate intraepithelial neoplasia (HG-PIN) and optional benign prostate hypertrophy (BPH) using green tea catechins.

BACKGROUND OF THE INVENTION

Numerous treatment options are known in the art for patients that are diagnosed with a condition that precedes prostate cancer. Most commonly, watchful waiting is preferred over open or transurethral surgery, or drug treatment. However, all of those options have various disadvantages and often fail to arrest progression of the condition to prostate cancer, or where progression is temporarily halted (e.g., using finasteride), prostate cancer tends to occur with some delay at a significantly higher grade. Still further, most known treatment methods are also largely ineffective in alleviating symptoms associated with BPH.

For example, WO 2005/092342 teaches a combination of a tailored alpha-1 adrenoceptor antagonist, which is selective for an alpha-1a over alpha-1b receptor subtype (but non-selective for alpha-1a over alpha-1d receptor subtype) with a muscarinic receptor antagonist and a further optional a 5-alpha-reductase inhibitor. Similarly, U.S. Pat. No. 6,200,573 teaches combinations of an alpha-1 adrenoceptor antagonist with a phytotherapeutic agent (e.g., Serenoa repens extract) for treatment of LUTS and BPH. Alpha-1 adrenoceptor antagonists are often relatively effective in reducing at least some of the symptoms associated with BPH, however, often produce various undesirable side effects due to their binding with other adrenoreceptor subtypes.

In other known examples, lonidamine and analogs thereof were reported as therapeutic agents for treatment and prophylaxis of BPH as disclosed in WO 2006/015283. However, such compounds typically inhibit cellular energy metabolism and affect testicular steroid hormone production and are thus not well tolerated over a prolonged period of time. To avoid at least some of the problems associated with lonidamine and related compounds, tadalafil and other inhibitors of type-5 phosphodiesterases can be used to treat the symptoms of BPH and LUTS as described in WO 2007/047282. While such inhibitors have a relatively favorable safety profile, comparably high cost of such compounds may preclude widespread use.

In still further known methods of treating BPH and other emiction disorders, numerous combinations of plant extracts (e.g., from ginseng, gingko, cassia twig, cinnamon, liquorices, etc.) were proposed, as for example, in U.S. Pat. App. No. 2005/0220904. Here, raw materials are decocted or extracted in an ethanol solution or water, and subsequently concentrated and dried for preparation of a therapeutic composition. Other known methods include use of a lignan preparation in combination with a second plant extract (e.g., isoflavone, tocopherol, phytosterol, polyphenol, catechin, or anthocyanin) to produce a composition that delays onset of prostate cancer as described in U.S. Pat. App. No. 2006/0234948. Furthermore, green tea has been reported in several models to accumulate in prostate tissue and to possibly prevent cancer (see e.g., J Nutr. 2006 July; 136(7):1839-43). Unfortunately, successful use of herbal remedies for treatment of prostate cancer has proven elusive, which was reiterated in the guide for making treatment decisions of the American Cancer Society ("While the results of lab studies have been promising, at this time the consensus of available scientific evidence does not support claims that green tea can help prevent or treat any specific type of cancer in humans").

Thus, while numerous compositions and methods of treating symptoms associated with HG-PIN and BPH are known in the art, almost all of them suffer from several disadvantages. Therefore, there is still a need for improved compositions and methods of treating symptoms associated with HG-PIN and BPH.

SUMMARY OF THE INVENTION

The present invention is directed to compositions and methods for reducing lower urinary tract symptoms (LUTS) in patients with an abnormal prostate, and especially in those diagnosed with HG-PIN with concurrent BPH. Most significantly, the inventors unexpectedly discovered that treatment success appears to be selectively associated with a single and specific progression state of prostate disease, and particularly with HG-PIN, typically with concurrent BPH.

In one aspect of the inventive subject matter, a method of facilitating a reduction of lower urinary tract symptoms (LUTS) in a patient includes a step of providing a catechin preparation and a further step of providing information that administration of the catechin preparation to a patient that is diagnosed with high-grade prostate intraepithelial neoplasia (HG-PIN) and coexistent benign prostate hyperplasia (BPH) is effective to reduce LUTS where administration is at a dosage effective to reduce LUTS. Viewed from a different perspective, contemplated methods of treating LUTS in a patient will therefore include a step of ascertaining a patient as having HG-PIN and coexistent BPH and a further step of administering a catechin preparation to the patient at a dosage effective to reduce LUTS.

In especially preferred aspects of contemplated methods, administration of the catechin preparation is not accompanied by a reduction of prostate volume, however, will in at least some cases lower serum prostate specific antigen (PSA). Most typically, administration of the catechin preparation also reduces progression of HG-PIN to prostate cancer. It is generally preferred that in contemplated methods a study will ascertain that administration of the catechin preparation reduces LUTS at least two points as measured by the International prostate symptom score (IPSS). Most typically, reduction in LUTS is reflected by improvement of at least two and more preferably at least three symptoms (e.g., incomplete emptying, frequency, intermittency, urgency, weak stream, straining, nocturia). Particularly preferred catechin preparations comprise at least 50 wt % EGCG, at least 6 wt % ECG, at least 10 wt % EC, and at least 3 wt % EGC, and will most typically comprise less than 1.5 wt % caffeine.

Various objects, features, aspects and advantages of the present invention will become more apparent from the following detailed description of preferred embodiments of the invention.

DETAILED DESCRIPTION

The inventors have unexpectedly discovered that the progression of high-grade prostate intraepithelial neoplasia (HG- PIN) to prostate cancer (PCa) can be effectively stopped or at least substantially delayed (e.g., >1 year) by stage-specific administration of catechin compounds, and especially compositions comprising EGCG, EGC, and/or ECG. Most remarkably, when the patient population for administration of such compounds was strictly limited to those diagnosed with HG-PIN (and did exclude all other stages of progression prior to prostate cancer), the progression to PCa was substantially completely halted in such patients whereas the control group not receiving such compounds progressed to PCa in the statistically expected numbers. A still further unexpected outcome of such treatment (particularly in the HG-PIN limited patient population) was the clear and significant decline in LUTS, and especially where the patient was also diagnosed with BPH.

Therefore, the inventors contemplate methods of facilitating a reduction of LUTS in a patient in which information is first provided that administration of the catechin preparation to a patient that is diagnosed with HG-PIN and optional coexistent BPH is effective to reduce LUTS (administration of such preparation is typically at or above a dosage effective to reduce LUTS). Most typically, a manufacturer, distributor, and/or merchant of a catechin preparation will disseminate the information in various manners. For example, where the catechin preparation is marketed as a prescription drug, provision of information may include a filing with the food and drug administration or other regulatory agency. On the other hand, where the preparation is marketed over the counter, provision of information may include a marketing flyer, a package description, an Internet ad, and/or sales display. Alternatively, or additionally, the information may also be provided via publication of a clinical study that reports the result. Therefore, suitable manners of providing information will include provision of printed, displayed, and electronically transmitted information. Thus, and viewed from a different perspective, a method of treating LUTS in a patient is also contemplated in which a physician or other health care professional (and in some cases even a lay person or the patient) ascertains that the patient has HG-PIN optionally with coexistent BPH. Once the disease status is confirmed, the catechin preparation is then (self-) administered to the patient at a dosage effective to reduce LUTS. HG-PIN is typically diagnosed by standard biopsy procedures well known in the art. However, alternative manners are also deemed suitable and include various non-invasive methods such as ultrasound or nuclear magnetic imaging techniques. Similarly, BPH can be diagnosed in numerous manners, however, is most preferably confirmed by ultrasound imaging. Therefore, it should be especially noted that administration of contemplated compounds is limited to a patient population and/or individual that has been positively diagnosed with HG-PIN (and optionally coexistent BPH), but not with a precursor form of HG-PIN or prostate cancer. Viewed from a different perspective, patients not diagnosed with HG-PIN (and optionally coexistent BPH) will not receive the catechin containing preparations contemplated herein.

In especially preferred aspects, the catechin preparation is a commercially available green tea extract that includes both galloylated and non-galloylated catechins, preferably in a ratio that is substantially identical (+/−10%) to the ratio naturally found in green tea. In alternative aspects of the inventive subject matter, the catechin preparation may also be modified such that only one (e.g., EGCG) or two (e.g., EGCG and EC) predominant compounds are present, which may be naturally occurring compounds or may be chemically modified compounds. For example, especially suitable natural compounds include EGCG, EC, EGC, while chemically modified compounds include those in which one or more substituents are added or replaced (e.g., galloyl ester bond replaced by amide bond, or one or more hydroxyl groups on the catechin esterified with acyl group).

Among other contemplated catechin preparations, particularly preferred preparations are those in which the catechins are present as a dry formulation for oral administration, wherein the preparation is produced from green tea. Such preparations may advantageously be decaffeinated and present in dosage units of between 100 mg and 1200 mg (with caffeine levels of less than 2 wt %, and more preferably less than 1.5 wt %). For example, suitable preparations will comprise at least 30 wt %, more typically at least 40 wt %, and most typically at least 50 wt % EGCG, at least 1 wt %, more typically at least 3 wt %, and most typically at least 6 wt % ECG, at least 3 wt %, more typically at least 6 wt %, and most typically at least 10 wt % EC, and at least 1 wt %, more typically at least 2 wt %, and most typically at least 3 wt % EGC. Of course, it should be noted that numerous of the commercially available preparations are also deemed suitable. Therefore, contemplated catechin preparations will also include liquid concentrates (relative to green tea) and parenteral compositions (typically for intramuscular or intravenous administration in a pharmaceutically acceptable carrier).

With respect to contemplated dosages, it is generally preferred to administer the catechin preparation orally at a daily dose of between 100 mg and 2400 mg, more typically between 200 mg and 1200 mg, and most typically between 400 mg and 800 mg. Depending on the daily dose, it should be noted that the catechin preparation may be administered in a single dose or in multiple doses, preferably distributed throughout the day. Therefore, two or three administrations per day at a total daily dose of about 600 mg is typically preferred. Moreover, it is contemplated that the catechin preparation can be administered prior to a meal (e.g., to increase catechin serum concentration) or with food (e.g., to reduce nausea, especially where the catechin is administered at a relatively high dose).

Clinical Trial Results

The following experimental data were obtained in a relatively small clinical trial in which 60 men were enrolled with informed consent. All trial participants were diagnosed has having HG-PIN (monofocal HG-PIN 17, plurifocal HG-PIN 13), most of them with coexistent BPH. Unless stated otherwise, all metrics are expressed in mean ±SD. The participants were randomly assigned to a placebo group and a treatment group, and treatment was carried out over a period of 12 months. In the treatment group, Polyphenon E (commercially available from Mitsui Norin, Japan) was administered 3 times daily at a total daily dose of 600 mg (3×200 mg), while the placebo group received a sugar pill using the same schedule. Examination after the conclusion of the treatment period revealed the following results.

At enrollment, men in the placebo group had an average age of 65.1±6.8 years and had a serum PSA level of 7.9±6.9. Prostate volume at the start of the trial was 49.9±21.5 ml, and at the end of the trial 50.0±21.8 ml (P value at 95% confidence: 0.813; end vs. enrollment). At enrollment, men in the treatment group had an average age of 64.4±5.9 had a serum PSA level of 7.6±3.8 (P value at 95% confidence 0.819; placebo vs. GTC). Prostate volume at the start of the trial was 49.0±19.8 (P value at 95% confidence 0.862; placebo vs. GTC), and at the end of the trial 48.3±19.5 (P value at 95% confidence 0.756; placebo vs. GTC). Statistical analysis (t-test analysis) showed that none of the variables considered were significantly different in the two arms of the study with 95% confidence (age, P=0.670; PSA, P=0.819; prostate volume at enrollment, P=0.862; prostate volume at end of study, P=0.756). Most remarkably, prostate volumes at the enrollment were not significantly different from those at the end of the study in placebo arm (P=0.813) or GTC arm (P=0.427). Such finding is even more unexpected as LUTS in the treatment arm significantly improved. In contrast, heretofore known pharmaceutical treatments (e.g., treatment with finasteride) result in shrinkage of the prostate, which in turn is thought to provide some relief from some of the symptoms.

To evaluate the LUTS improvement and quality of life improvement, all participants were asked to provide information using the standardized IPSS Questioinnaire (International Prostate Symptom Score; J Urol 1992 November; 148 (5):1549-57) together with a quality of life score as shown below. Total score was obtained by adding number of points of all answers.

|  | Initial IPSS | 3 month IPSS | P | % with Reduction | Initial QoL | 3 month QoL | P | % with Reduction |
|---|---|---|---|---|---|---|---|---|
| Placebo | 8.27 | 7.00 | 0.14 | 46 | 1.30 | 1.47 | 0.27 | 7 |
| Catechin | 11.12 | 9.12 | 0.04 | 65 | 2.06 | 1.76 | 0.08 | 35 |

As can be seen from the table above, the reduction in LUTS as well as the improvement of the quality of life was not only statistically significant but also widespread throughout the treatment group. In most participants, administration of the catechin preparation reduced LUTS at least two points as measured by the International prostate symptom score. Furthermore, in most participants, administration of the catechin preparation also reduced the score in at least two and more typically three symptoms (such as incomplete emptying, frequency, intermittency, urgency, weak stream, straining, and nocturia), which is a significant improvement over the control

| IPSS Questionnaire | | | | | | |
|---|---|---|---|---|---|---|
|  | Not at all | Less than 1 time in 5 | Less than half the time | About half the time | More than half the time | Almost always |
| Incomplete emptying: Over the past month, how often have you had a sensation of not emptying your bladder completely after you finish urinating? | 0 | 1 | 2 | 3 | 4 | 5 |
| Frequency: Over the past month, how often have you had to urinate again less than two hours after you finished urinating? | 0 | 1 | 2 | 3 | 4 | 5 |
| Intermittency: Over the past month, how often have you found you stopped and started again several times when you urinated? | 0 | 1 | 2 | 3 | 4 | 5 |
| Urgency: Over the last month, how difficult have you found it to postpone urination? | 0 | 1 | 2 | 3 | 4 | 5 |
| Weak stream: Over the past month, how often have you had a weak urinary stream? | 0 | 1 | 2 | 3 | 4 | 5 |
| Straining: Over the past month, how often have you had to push or strain to begin urination? | 0 | 1 | 2 | 3 | 4 | 5 |
| Nocturia: Over the past month, many times did you most typically get up to urinate from the time you went to bed until the time you got up in the morning? | None 0 | 1× 1 | 2× 2 | 3× 3 | 4× 4 | ≧5× 5 |

| Quality Of Life Due To Urinary Symptoms | | | | | | | |
|---|---|---|---|---|---|---|---|
|  | Delighted | Pleased | Mostly satisifed | equally satisifed and dissatisfied | Mostly dissatisfied | Unhappy | Terrible |
| If you were to spend the rest of your life with your urinary condition the way it is now, how would you feel about that? | 0 | 1 | 2 | 3 | 4 | 5 | 6 |

Most participants in the treatment group had a reduction in at least two or three of the listed symptoms at at least 1-2 points. In contrast, no significant change was observed in the placebo group at the end of the trial:

group. Once more, it should be noted that such improvements were not accompanied by a significant reduction in total prostate volume, however, were accompanied by a relatively small decrease in serum PSA reaching near significant level.

Of particular additional significance is the observation that administration of the catechin preparation effectively arrested progression of HG-PIN to PCa as compared to the placebo group in which PCa incidence at the 12 month mark was substantially the same as expected (about 30% of men will generally progress from HG-PIN to PCa within 1 year without treatment). Further specific details, additional embodiments, and contemplations are disclosed in our publication (Cancer Res. 2006; 66:(2), pages 1234-1240) and U.S. national phase of PCT application with the serial number PCT/IB2005/002107, both of which are incorporated by reference herein.

Thus, specific embodiments and applications of compositions and methods related to stage-specific reduction of LUTS have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification and contemplated claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of reducing symptomatology associated with benign prostate hyperplasia (BPH) in a human patient, comprising:
   administering a catechin preparation;
   wherein administration of the catechin preparation is specific to a patient that is diagnosed with high-grade prostate intraepithelial neoplasia (HG-PIN) and coexistent benign prostate hyperplasia (BPH), and wherein administration is performed under a protocol that is effective to reduce the symptomatology associated with BPH and to reduce progression of HG-PIN to prostate cancer; and
   wherein the catechin preparation comprises at least 50 wt % epigallocatechin gallate (EGCG), at least 3 wt % epicatechin gallate (ECG), at least 3 wt % epicatechin (EC), and at least 3 wt % epigallocatechin (EGC).

2. The method of claim 1 wherein the administration of the catechin preparation is not accompanied by a reduction of prostate volume.

3. The method of claim 1 wherein the administration of the catechin preparation lowers serum prostate specific antigen (PSA).

4. The method of claim 1 further comprising a step of ascertaining in a study that the administration of the catechin preparation reduces the symptoms at least two points as measured by the International prostate symptom score (IPSS).

5. The method of claim 1 wherein reduction in symptomatology includes improvement of at least two symptoms selected from the group consisting of incomplete emptying, frequency, intermittency, urgency, weak stream, straining, and nocturia.

6. The method of claim 1 wherein reduction in symptomatology includes improvement of at least three symptoms selected from the group consisting of incomplete emptying, frequency, intermittency, urgency, weak stream, straining, and nocturia.

7. The method of claim 1 wherein the administration of the catechin preparation comprises oral administration at a daily dose of between 400 mg and 1200 mg.

8. The method of claim 1 wherein the catechin preparation comprises less than 1.5 wt % caffeine.

* * * * *